United States Patent

Lemchen

[11] Patent Number: 6,081,739
[45] Date of Patent: Jun. 27, 2000

[54] SCANNING DEVICE OR METHODOLOGY TO PRODUCE AN IMAGE INCORPORATING CORRELATED SUPERFICIAL, THREE DIMENSIONAL SURFACE AND X-RAY IMAGES AND MEASUREMENTS OF AN OBJECT

[76] Inventor: Marc S. Lemchen, 553 Park Ave., New York, N.Y. 10021

[21] Appl. No.: 09/083,331

[22] Filed: May 21, 1998

[51] Int. Cl.[7] .......................................................... A61B 6/00
[52] U.S. Cl. .............................................................. 600/407
[58] Field of Search ..................................... 600/407, 440, 600/443, 444, 445, 447; 250/363.04, 363.03

[56] References Cited

U.S. PATENT DOCUMENTS

| | | |
|---|---|---|
| 3,652,852 | 3/1972 | Miyazawa et al. . |
| 4,521,688 | 6/1985 | Yin . |
| 4,672,651 | 6/1987 | Horiba et al. . |
| 4,908,843 | 3/1990 | Gall et al. . |
| 4,920,573 | 4/1990 | Rhodes et al. . |
| 4,939,761 | 7/1990 | Gall et al. . |
| 4,979,203 | 12/1990 | Suckewer et al. . |
| 5,117,446 | 5/1992 | Haaker et al. . |
| 5,136,627 | 8/1992 | Conrads et al. . |
| 5,177,779 | 1/1993 | Cornu et al. . |
| 5,251,635 | 10/1993 | Dumoulin et al. . |
| 5,299,253 | 3/1994 | Wessels . |
| 5,391,877 | 2/1995 | Marks . |
| 5,410,144 | 4/1995 | Lavelle et al. . |
| 5,519,225 | 5/1996 | Mohr et al. . |
| 5,523,791 | 6/1996 | Berman . |
| 5,585,637 | 12/1996 | Bertelsen et al. . |

Primary Examiner—Scott M. Getzow
Attorney, Agent, or Firm—Daniel L. Dawes

[57] ABSTRACT

A conventional digital panoramic radiographic unit includes sonic or optical three dimensional scanning detector and a color video detector so that when the panoramic x-ray data is obtained, three dimensional contour of the surface of the patient's skin and the outward visual appearance of the patient's skin are also obtained as correlated data sets. The correlated data sets are then stored within a computer system as three sets of simultaneously or near simultaneously taken correlated data. The correlated data is then deconvolved to form a two-dimensional image of the tooth and jaw structure of patient as correlated to the patient's jaw and lip contours and visual appearance from a selected viewpoint.

15 Claims, 3 Drawing Sheets

SCANNING DEVICE OR METHODOLOGY TO PRODUCE AN IMAGE INCORPORATING CORRELATED SUPERFICIAL, THREE DIMENSIONAL SURFACE AND X-RAY IMAGES AND MEASUREMENTS OF AN OBJECT

BACKGROUND OF THE INVENTION

1. Field of the Invention

The invention relates to the field of measurement and visualization of the superficial surface appearance, three dimensional contour and subsurface structure of an object, and in particular to improvements in orthodontics and oral surgery in measuring and visualizing anatomical landmarks used in orthodontic analysis by direct measurement of the face, head and jaws of a subject to produce correlated video, laser and x-ray derived measured images and to topologically transform the same to hypothetical modifications for visualization.

2. Description of the Prior Art

The apparatus for generating cephalometric tracings directly from a patient by generating digitized two or three dimensional data from a patient's head from defined locations of preselected landmarks is well known and is based on the use of optical or sonic marking using three dimensional triangulation. For example, such an apparatus is shown and described in Lemchen, et al. "Method and Apparatus for Generating Cephalometric Images," U.S. Pat. No. 5,278,756 (1994) in which a means for defining a position with respect to a given anatomical reference is provided by a probe having a tip which generates signals of a certain optical or sonic frequency, when activated when positioned at selected reference points on the head or jaw. Triangulation detectors receive the position indicating signals from the probe and a computer processes the received signals to provide digital data corresponding to the three dimensional location of the probe tip with reference to the head or jaw. A visual image of the head or jaw is displayed as seen from a chosen direction or directions with a video camera. The video image is displayed together with a cephalometric tracing as would be seen in the same direction and scale which tracing is derived by joining appropriate anatomical landmarks with tracing lines generated by the computer according to any one of a number of accepted tracing techniques.

Lateral cephalograms using x-ray exposures are also well known from conventional orthodontic diagnosis. One prior art system for computer generating lateral cephalometric tracings is described in Ricketts, et al., "Orthodontic Diagnosis and Planning" as published by Rocky Mountain Orthodontics of Denver, Colo. (1982).

Panoramic radiography is also well established and has recently been commercialized to create digitized x-ray panographs as, for example, as provided by the system sold under the trademark, Siemens SIDEXIS, as manufactured by Pelton & Crane of Charlotte, N.C. Digitized x-ray signals are received directly from the panographic exposure and real time processing enables immediate display of the x-ray images on a monitor.

However, the panographic gantry and exposure equipment operates solely in connection with a single x-ray exposure and image. The laser optical or sonic equipment described in U.S. Pat. No. 5,278,756 also operates solely in relationship to a single detection and imaging system. The data from the separate x-ray panograph and the optical or sonic cephalometric trace can be downloaded into a single computer and through nontrivial and substantial computing effort with some degree of programming skill, the two sets of data can be correlated after the fact. However, such an approach requires multiple exposure apparatus, and considerable time and computer operator skill in order to obtain usefully correlated x-ray and laser images.

Marks, "Combined Imaging Scanner," U.S. Pat. No. 5,391,877 (1995) describes an image scanner that combines images obtained from two systems that are supported on a combined gantry. The Single Photon Emission Computed Tomographic (SPECT) Scanner includes a gantry supporting a computed tomographic (CT) Scanner 12. The gantry also supports the SPECT Scanner 14. The single table 16 supporting the patient's position sequentially pass through both gantries. Initially the CT data is obtained and then the SPECT data. The single computer 18 mathematically convolves the two image data sets. The CT data is processed to provide a background or map on which to superimpose the SPECT data. As The CT anatomical data is convolved with the SPECT radioisotope distribution data to provide a color-shaded relief image. A single computer 18 is used for the analysis. The information is displayed on a machine control display 20, a raw CT display terminal 22, and a raw SPECT display terminal 24 and a combined CSPECT display terminal 26. Image on the display terminal 26 can be printed to a color laser printer 28.

Wessels, "Alignment System to Overlay Abdominal Computer Aided Tomography and Magnetic Resonance Anatomy With Single Photon Emissions Tomography," U.S. Pat. No. 5,299,253 (1994) describes a system comprised of machine-base support means: (a) with a contrasting marker means (b) attached to the support for providing a set of markings which uniquely identifies a cross-section of an imaged object. The support means includes material encasement, and means to encapsulate the contrasting markers in an inert material. The material for the encasement may be polymer, wood, foam, metal, ceramic or a combination of these materials which do not otherwise interfere with the imaging system. Contrasting marker (b) is a mark whose outline can be accurately viewed without distortion or blurring within the image system being used. The marker can have many shapes including that of a solid or hollow tube. The contrast agent in the marker is a solid, liquid or gas which is readily discernible with a particular type of imaging system used. The pattern of contrast markers must be such that there is at least one transversely constant contrast marker and at least one transversely variable contrast marker spanning the longitudinal and imaging area. The alignment system can be used in one plane, or there can be a series of alignment systems in planes above the object to be imaged. In use, for registering single photon emission tomography images with computer tomography or magnetic resonance images, the object to be imaged placed on a support means. The support means can be a partial cast of the object's external shape. At least a portion of the object is adjacent to a contrast marker means. The object is imaged using two or more imaging techniques. At least two images of the object are registered to produce a coherent image of the object.

Mohr, et al., "System and Method For Using A Dual Modality Detector For Inspecting Objects," U.S. Pat. No. 5,519,225 (1996) describes an industrial inspection system using a dual modality gas ionization detector with beams of either neutrons or photons from X-rays or gamma rays passing through the object. A dual modality gas ionization detector 10 has a window 16 for transmitting X-rays or gamma rays. The windows is made of a material which is permeable to these types of radiation. The detector includes a housing 12 that has an ionization chamber 18 filled with high pressure gases such as helium or Xe, which chamber 18 is used to detect the neutron, x-ray or gamma rays fluxes incident on the ionization detector.

The inspection system is used to detect the presence of nitride and titanium sponge nuggets or residual core material in hollow-cast turbine engine blades. Mohr was cited for showing the simultaneous irradiation of objects with two types of radiation and the simultaneous and alternating detection of the same. The structure of the Mohr device includes a collimator 20 comprised of two bars 22 and 24 define a slit 26 between them which collimates the beams entering the chamber into a thinner beam. The beams entering the chamber interact with gases to produce a secondary-ionization charge that has accelerated toward electrodes 28. A single layer of nuggets 34 on conveyor belt 40 are imaged by moving past a dual radiation source 42, which alternately pulses neutrons and X-rays or gamma rays at the nuggets. The dual modality gas ionization detector 10 measures the transmissivity of the alternating radiation passing through the nuggets and supplies a signal to image generator 46. Image generator 46 includes an analog digital converter 48, processing means 50 and an image display device 52.

Dumoulin, et al., "*Stereoscopic X-Ray Fluoroscopy System using Radiofrequency Fields*," U.S. Pat. No. 5,251,635 (1993). The system is directed to minimizing an X-ray dose while still providing a stereoscopic tracking image of an invasive device in a patient. FIG. 1 shows a patient 112 positioned in the X-ray imaging system. The system provides a stereoscopic view of the patient with the X-ray image being only occasioned updated. The computer system tracks the invasive device and provides a superimposed image of the evasive device with the position being updated at a high rate. The invasive device has a transmitter coil that transmits an RF signal to a plurality receiving coils placed around the patient. The tracking computer calculates the position and orientation of the invasive device and supplies the image superpositioned on the last X-ray image. The tracking system can be used with other imaging systems such as magnetic resonant scanners, ultra sound scanners, positron emission, tomography scanners and the like.

Suckewer, et al., "*X-Ray Laser Microscope Apparatus*," U.S. Pat. No. 4,979,203 (1990) describes an X-ray contact microscope and optical phase contrast microscopic system. Object cells 22 have been cultured on an X-ray resist surface 46. An inverted microscope 26 using light source 34 is used to position the object cells for exposure to a soft X-ray beam 30 from an x-ray laser source 200. An ultraviolet light source 66 is provided to monitor fluorescent effects of the object.

None of the prior art references show a multiple scanning exposure system for dental application in which the dental X-ray is separately created and combined with video and laser scanning of a patient's face or jaw structure.

None of the systems are concerned with combinations which would combine surface data, and in particular, facial surface data, with underlying bone structural data derived from X-ray scans. The correlation between underlying bony structure and outward superficial tissues is a correlation which is qualitatively and conceptually different than correlation or alignment between different scans of the same internal structure.

What is needed is some type of apparatus and methodology whereby multiple scanned cephalometric or dental images can be conveniently, economically and quickly combined for usefully correlated result.

BRIEF SUMMARY OF THE INVENTION

The invention is an apparatus for simultaneously providing multiple scans of measured data from a patient comprising a plurality of scanning devices for providing the multiple scans of measured data from the patient, and a scanning gantry in which the plurality of scanning devices are mounted at least in part for scanning the patient. A computer system or workstation correlates the output from each of the multiple scanning devices to provide at least a composite image of the patient attained therefrom in which the measure data of the multiple scans are correlated to each other.

In the illustrated embodiment the scanning gantry rotates at least in part about a portion of interest of the patient. The scanning gantry rotates about the lips, teeth and jaw structure of the patient.

The plurality of scanning devices includes an x-ray exposure device, such as a panoramic x-ray exposure device or a teleradiographic x-ray exposure device.

The plurality of scanning devices also includes a video imaging device, and preferably a color video imaging device.

The plurality of scanning devices still further includes a three dimensional scanning device.

In the preferred embodiment each of the plurality of scanning devices acquires data simultaneously and simultaneously stores the multiple data in the computer system as correlated data. It is also contemplated that the plurality of scanning devices acquire data in sequence doing a single exposure session of the patient and stores the sequentially acquired data as correlated within the computer system.

In particular, the plurality of scanning devices acquires tooth and jaw structure data in a first scanning device, three dimensional contour data through a second scanning device and superficial surface data through a third scanning device. The same scanning device may collect more than one of the data sets if desired. The tooth and jaw structure, three dimensional contour data and superficial surface data are correlated by the computer system to provide a composite image thereof.

The invention is also a method of creating correlated multiple scans of a patient to correlate bone structure to skin contour and to surface appearance comprising imaging a bone structure, skin surface contour and skin surface image of a patient by correlated multiple scans of the same. The skin surface image may be in color and the skin surface contour may use any type of three dimensional display representation desired such as mesh net images, contour lines or shading. The multiple scans of correlated data are simultaneously displayed to produce a composite image.

The invention having now been briefly summarized, can be better visualized by turning to the following drawings wherein like elements are referenced by like numerals.

The invention and its various embodiments, now having been briefly summarized and visually depicted in the foregoing drawings, can be understood by turning to the following detailed description.

DETAILED DESCRIPTION OF THE PREFERRED EMBODIMENTS

A conventional digital panoramic radiographic unit includes sonic or optical three dimensional scanning detector and a color video detector so that when the panoramic x-ray data is obtained, three dimensional contour of the surface of the patient's skin and the outward visual appearance of the patient's skin are also obtained as correlated data sets. The correlated data sets are then stored within a computer system as three sets of simultaneously or near simultaneously taken correlated data. The correlated data is then deconvolved to form a two-dimensional image of the tooth and jaw structure of patient as correlated to the patient's jaw and lip contours and visual appearance from a selected viewpoint. Additional scans may be added as correlated data sets, such as three-dimensional surface scans of the teeth for orthodontic purposes.

Figure 1:
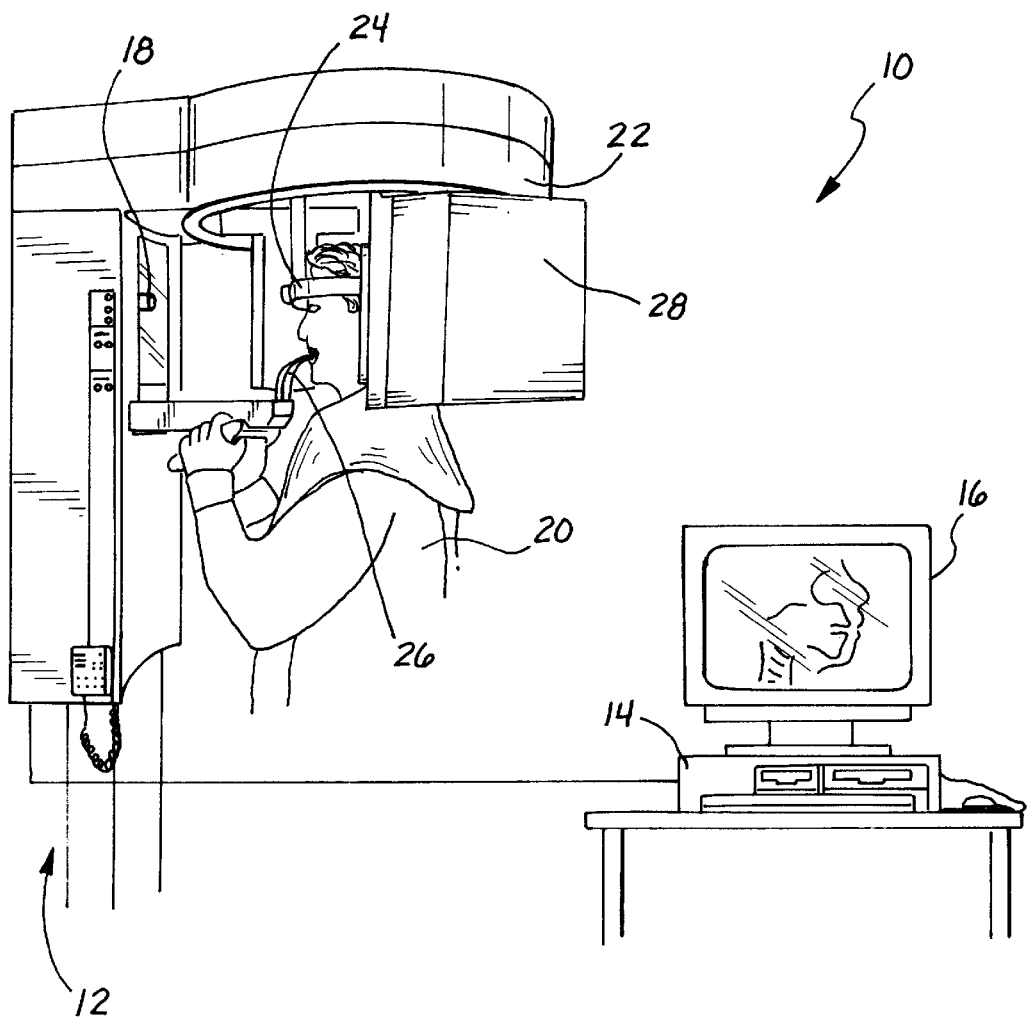
FIG. 1 is a side perspective view of a digital dental topography panoramic device which includes x-ray scanning, laser or sonic cephalometric tracing and video imaging in a single real time mechanism.

FIG. 1 is perspective side view of the apparatus, generally denoted by reference numeral 10, which is a device for providing panoramic dental digital tomography in a manner similar to digital radiology devices such as sold under the trademark, Siemens SIDEXIS, by Pelton and Crane of Charlotte, N.C. Apparatus 10 is comprised generally of a console 12 which includes a computer 14 to which is connected a monitor 16 and video camera 18. Console 12 also includes an x-ray source and control circuitry for the x-ray source (not shown) for the purpose of providing a controlled x-ray exposure of a patient 20 positioned within a panoramic gantry 22. The patient's head is maintained stationary at a fixed position by means of a head brace 24 and the jaw is maintained in a fixed partially part separation by means of a jaw bite fixture 26. A rotating detector 28 rotates about the patient's head to obtain a digitized real time x-ray topographic image of the patient's teeth and jawbone structure.

Figure 2:
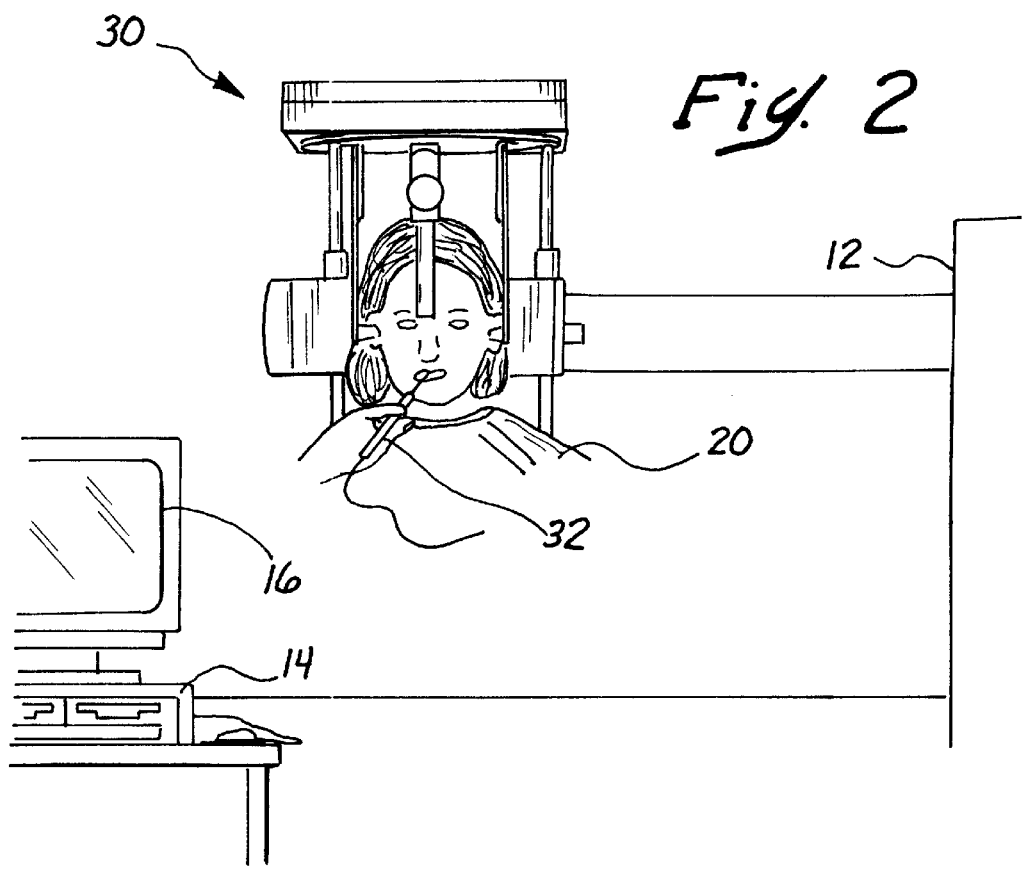
FIG. 2 is a depiction of utilization of the device of FIG. 1 in which the anatomical landmarks are being optically or sonically marked.

It must be clearly understood that the configuration of the device shown in FIG. 1 is only illustrative and is not limiting to the scope of the invention. Many other types and configurations of scanning systems could be employed, which are now known or may be later devised which would be equivalent to the SIDEXIS in one or more of its features. The feature of the system of FIGS. 1 and 2 which is relevant to the invention is that it is suitable for providing dental exposures of x-rays, three dimensional imaging or scanning and superficial images in a single gantry or scanning mechanism shared by all of the exposure and detection elements.

Device 10 can also be reconfigured to provide teleradiography by means which is conventional and thus will not be further discussed here. The point is that the scanning mechanism used in the invention may be of any type now known or later devised to create any desired dental or orthodontic images and is not just moving direction images like panoramic radiographs or fixed direction images like teleradiographs. The teleoradiographic unit 30 is depicted in the perspective view of FIG. 2. Different radiographic programs as well as immobilization fixtures can be utilized in the apparatus and methodology of the invention, again without limitation to what is illustrated here. For example, 16 different radiographic programs for diagnosis of the jaw region of patient 20 are conventionally included within the panoramic videographic apparatus 10 in the SIDEXIS system. However, it is expressly understood that the invention is not limited by the modalities of operation of panoramic radiographic devices currently available or as made later available, but includes within its scope any type of digitized x-ray diagnostic equipment.

At the same time that the panographic radiograph of patient 20 is being taken by apparatus 10, video camera 18 of apparatus 10 also is taking a real time corresponding or correlated video image of the patient's face and in particular, that portion of the head relating to the patient's lips and jaw structure or teeth. The video imaging system may be of the type shown in U.S. Pat. No. 5,278,756, which is incorporated herein by reference, or may be any type of imaging system now known or later devised which can provide a digitized or digitizable image of the surface of the patient's head, face, jaw and/or lips, and teeth.

In the preferred embodiment the three dimensional color scanning system of Cyberware of Monterey, Calif., is used to provide both the superficial color image of the face, jaw, lips and teeth, and the three dimensional contours of the face, jaw, lips and teeth. The dentist or oral surgeon is thus able to work with true human faces by obtaining images as little as 12 seconds. The Cyberware Model WB4 whole-body scanner allows capture of the shape and color of the entire human body. To capture the intricacies of the human body in one pass, the scanner uses one or more scanning instruments mounted in apparatus 10. A linear ball-bearing rail and servo motor assembly may be used to move the scanning instrument in the desired directions or the rotating gantry of the SIDEXIS may be employed. The use of multiple scanning instruments improves accuracy on the sides of the face or body and in difficult-to-reach areas. The WB4 scans a cylindrical volume 2 meters (79 inches) high with a diameter of 1.2 meters (47 inches). These dimensions accommodate the vast majority of human subjects. For even larger subjects, available zippering software enables two or more scans to be quickly combined into a complete three dimensional color model.

The scanner is controlled via Cyberware software running on a Silicon Graphics workstation. Cables connect each scanning instrument to a SCSI controller unit and a power supply unit. The SCSI controllers connect to the workstation, which automatically collects the measurements into a complete three dimensional model. Graphics tools allow the scanned model to be viewed within seconds after completing a scan.

The three dimensional color digitizer, such as Cyberware's Model 3030, scans an object at high resolution in less than a minute and shows the resulting three dimensional image on a graphics workstation with true-to-life color. The availability of color information to three dimensional digitizing provides nearly all the information a graphics application needs to fully describe an object. In addition to enhancing realism in graphic models, color denotes boundaries that are not obvious from shape alone. Color indicates surface texture and reflectance. By marking by any visible means available an object's surface before digitizing, color can be used to transfer ideas from the object to the graphic model. In specialized applications, color can reveal characteristics such as skin discoloration.

The digitizer is entirely software controlled, and requires no user adjustments in normal use. In operation, the digitizer shines a safe, low-intensity laser on an object to create a lighted profile. A high-quality video sensor captures the profile from two viewpoints. The system can digitize thousands of these profiles in a few seconds to capture the shape of the entire object.

Simultaneously, a second video sensor acquires color information.

The scanning process captures an array of digitized points, with each point represented by x, y, and z coordinates for shape and 24-bit RGB coordinates for color. The digitizer transfers this data via SCSI to a graphics workstation for immediate viewing and modification.

The digitizer operates under the control of software running on a graphics workstation. The scanning process is thus automatic and easily adaptable to a variety of different requirements. Either rectangular or cylindrical scans can be performed depending on the shape of the object to be scanned. Multiple scans of a complex object can be combined into one model.

Software tools available from Cyberware allow manipulation and analysis of the three dimensional models in a variety of ways. Automatic measurement attributes such as area and volume can be obtained of selected portions of the three dimensional image. The models can be edited with operations such as clipping, scaling, and image cut and paste.

Popular third-party multimedia programs from Autodesk, Wavefront, and Alias, for example to work with the three dimensional models. Translation tools are available that convert the data array to a form readable by many third-party programs. Special-purpose translation routines may be custom created by the user. A feature extraction tool prepares three dimensional models for use in computer-aided design and other applications.

The scanner includes a completely self-contained optical digitizing head. It includes a low-intensity laser light source; quartz-coated, first-surface mirror assembly; high-quality imaging optics; 100% blemish-free, CCD (solid-state) video range and color sensors; and supporting electronics.

In an alternative embodiment after the x-ray, surface and contour images of the patient's head has been taken by the digitizer describe above, it is then possible to use a light or sonic handheld probe 32 such is described in connection with U.S. Pat. No. 5,278,756 to identify anatomical landmarks in the patient's jaw structure and/or face while the patient is still maintained in the exposure position as shown in FIG. 1 to include in a combined graphic model. Again, the specific means by which the anatomical tooth and jaw structure of the patient are determined through optical laser means need not be identical or even the same as discussed in connection with U.S. Pat. No. 5,278,756, but may include any type of three dimensional spatial orientation apparatus and methodology now known or later devised. In particular, patient landmarks may be made by the surgeon or orthodontics in the graphically displayed data itself by computer marking a point in the displayed image with a marker using a computer mouse or pen. The land-marked points can then be specifically used in later applied, conventional data reductions methodologies to compute tracings or to provide keystone points which will be moved or rotated according to expected orthodontics or oral surgery to provide a morphed image.

The object of the invention is that a real time visual or color video scan of the superficial facial and jaw structure of the patient is taken at the same time or at least at a time thereafter in which the patient is still in the same position and apparatus 10 has taken a panographic x-ray exposure and image. Three sets of data, one corresponding to the panographic x-ray, one corresponding to the facial color video image, and another corresponding to the optically identified anatomical landmarks are then established in the exposure space at or within the time of a single exposure session so that the data can be correlated before rendition of the display of each of the sets of data and preferably, but not necessarily, at the same time each set of data it is obtained through the use of a single mechanical scanning stage or mechanism.

Figure 3:
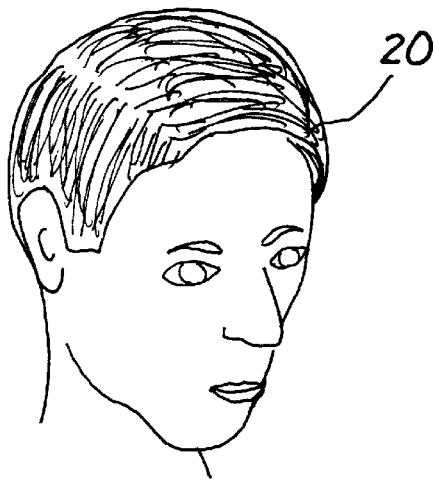
FIG. 3 is a perspective depiction of a video image of the surface of a patient taken with the device of FIGS. 1 and 2.

For example, FIG. 3 diagrammatically illustrates patient 20 as would be seen in a color video image of the patient's face showing the superficial parents of the teeth, lips, chin and jaw structure as would be commonly be seen by an observer.

Figure 5:
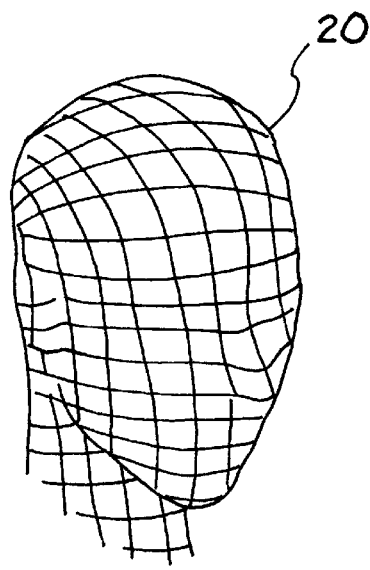
FIG. 5 is a laser contour of the anatomical landmarks of the patient taken in the device of FIGS. 1 and 2.

In FIG. 5, the optically determined three dimensional physical contour of the patient's face, and in particular the lips, and selected anatomical landmark positions within the patient's jaw structure or teeth are established in three dimensional space. Any depiction of the topology of the patient's face may be employed such as a mesh-net representation or topological contour or elevation lines.

Figure 4:
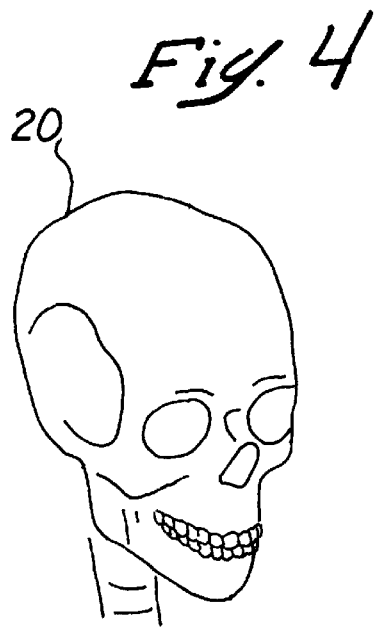
FIG. 4 is a panographic x-ray of the teeth and jaw bone of a patient taken in the device of FIGS. 1 and 2.
Figure 6:
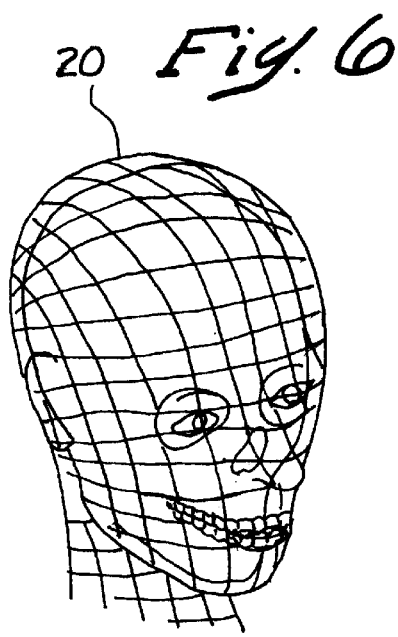
FIG. 6 is a superposition of the three scans depicted in FIGS. 3, 4 and 5 taken in real time in the device of FIGS. 1 and 2.

In FIG. 4 the panographic x-ray of the teeth and jaw structure of the patient in digitized form is depicted. These three images, which may be scanned simultaneously or at least within the same exposure session can then be point by point correlated or superimposed on each other in order to obtain a composite image such as shown in FIG. 6. It should become readily apparent that the composite image allows the orthodontic surgeon to quickly and readily visualize the relationship between jaw and tooth structure on one hand and facial lip and jaw contours, landmarks and superficial visual appearance on the other. The format and resolution of each of the sets of data may be the same or different from each other and from the display of the set of data according to user convenience and choice.

Through three dimensional computer morphed techniques, using conventional software, it is then possible to move or change tooth or jaw structure positions and according to user selection. A corresponding three dimensional contours which have a scanned or measure relationship to the original x-ray data will be carried in the image with the x-ray data resulting in a morphed or altered composite display of FIG. 6. The composite display can of course be deconvolved into any one of its constituent parts as shown in FIGS. 3, 4 and 5 according to user selection as may be needed or desired for visualization.

Figure 7:
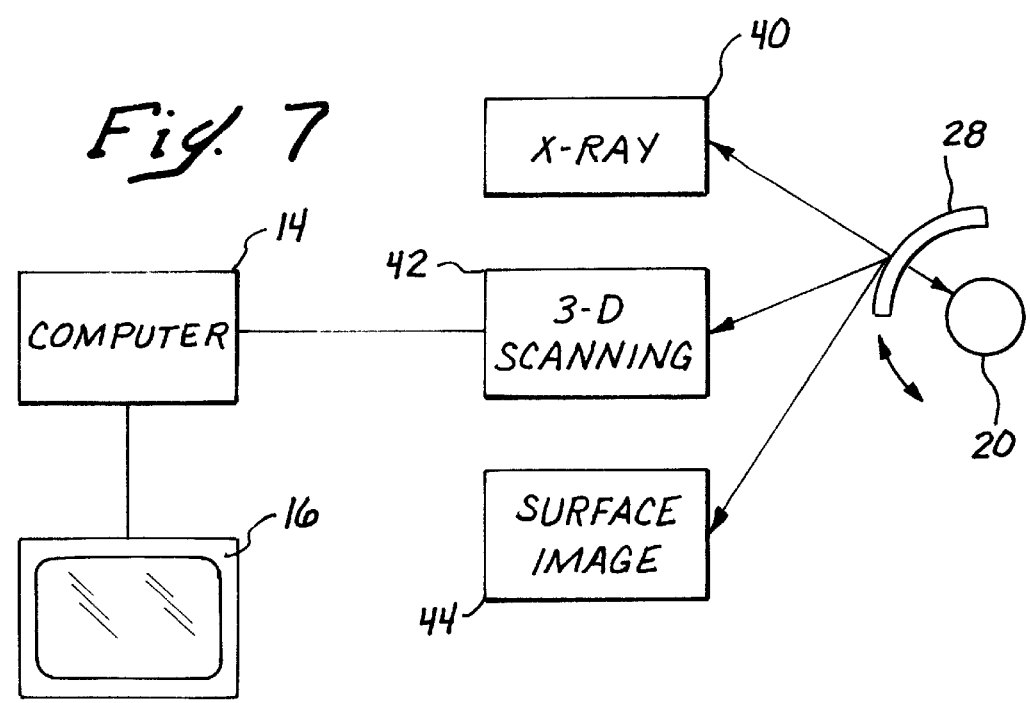
FIG. 7 is a block diagram of the invention which shows an X-ray exposure and detection system carried by gantry with a three dimensional contours scanning system and a surface image scanning system.

FIG. 7 is a block diagram of the system 10 of the invention which shows an X-ray exposure and detection system 40 carried by gantry 28 with a three dimensional contours scanning system 42 and a surface image scanning system 44. X-radiation, light, sonic energy is thus swept over patient 20 and the data simultaneously or near simultaneously provided in a correlated fashion to computer system 14 in which the three sets of data from systems 40, 42 and 44 are stored in a correlated fashion. Thereafter, computer 14 may display the image of patient 20 by any one of scanning systems, 40, 42 and 44 and further provide a composite image of each of these systems. Most importantly, data taken by one system is correlated to the data in another system as determined by the initial measurement. Therefore, later when the operator through conventional computer graphing techniques morphs the data in any one set, the data in the other two sets can similarly be morphed in the same manner to obtain a correlated separate or composite image. In this way, surgical or orthodontic changes in the tooth or bone structure can be computer simulated and the contour and visual appearance of the patient's lips, teeth and jaw will be immediately correlated thereto and displayed in monitor 16.

It must be expressly understood that more than or less than three data scanning systems may be employed to produce correlated data sets for orthodontic or oral surgery purposes, and there is no restriction under the invention as to what type of scanning mechanism or measurement signal might be employed.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims.

It is to be expressly understood that the scanning, exposure, detection, computer, and software components of the invention which have been specifically described above are not to be read as limiting the invention, which is to include all known or later devised methods and apparatus for performing the same or similar functions in the dental and orthodontic fields.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

I claim:

1. An apparatus for simultaneously providing multiple scans of measured data from a patient comprising:

a plurality of scanning devices for providing said multiple scans of measured data from said patient;

a scanning gantry in which said plurality of scanning devices are mounted at least in part for scanning said patient; and a computer system for correlating output from each of said multiple scanning devices to provide at least a composite image of said patient attained therefrom in which said measure data of said multiple scans are correlated to each other, wherein said plurality of scanning devices acquires subsurface structural data from said patient by at least a first scanning device and surface data from said patient by at least a second scanning device, said subsurface structure data and surface data from said patient being correlated by said computer system to provide a composite image of subsurface structural data and surface data of said patient.

2. An apparatus for simultaneously providing multiple scans of measured data from a patient comprising:

a plurality of scanning devices for providing said multiple scans of measured data from said patient;

a scanning gantry in which said plurality of scanning devices are mounted at least in part for scanning said patient; and a computer system for correlating output from each of said multiple scanning devices to provide at least a composite image of said patient attained therefrom in which said measure data of said multiple scans are correlated to each other;

wherein said plurality of scanning devices acquires tooth and jaw structure data in a first scanning device, three dimensional contour data through a second scanning device and superficial surface data through a third scanning device, said tooth and jaw structure, three dimensional contour data and superficial surface data being correlated by said computer system to provide a composite image thereof.

3. The apparatus of claim 2 wherein said first scanning device of said plurality of scanning devices includes an x-ray exposure device.

4. The apparatus of claim 2 wherein said first scanning device of said plurality of scanning devices includes a panoramic x-ray exposure device.

5. The apparatus of claim 2 wherein said first scanning device of said plurality of scanning devices incorporates a teleradiographic x-ray exposure device.

6. The apparatus of claim 2 wherein said third scanning device of said plurality of scanning devices includes a video imaging device.

7. The apparatus of claim 2 wherein said second scanning device of said plurality of scanning devices includes a three dimensional scanning device.

8. The apparatus of claim 2 wherein each of said plurality of scanning devices acquires data simultaneously and simultaneously stores said multiple data in said computer system as correlated data.

9. The apparatus of claim 2 wherein said plurality of scanning devices acquires data in sequence doing a single exposure session of said patient and stores said sequentially acquired data as correlated within said computer system.

10. The apparatus of claim 2 wherein said data from said first, second and third scanning devices is taken simultaneously.

11. The apparatus of claim 2 wherein said data taken from said first, second and third scanning devices is taken with respect to one of said scanning devices sequentially during the same exposure session of said patient.

12. A method of creating correlated multiple scans of a patient to correlate bone structure to skin contour and to surface appearance comprising:

imaging a bone structure, skin surface contour and skin surface image of a patient by correlated multiple scans of the same; and simultaneously displaying said multiple scans of correlated data to produce a composite image.

13. The method of claim 12 where said imaging occurs simultaneously with respect to each of said correlated scans.

14. The method of claim 12 wherein said imaging occurs at least in part sequentially with respect to said correlated scans at the same patient session.

15. The method of claim 12 wherein said imaging acquires panoramic x-ray data simultaneously with three dimensional contour of a patient's lips, teeth and jaw structure with simultaneous surface images of a patient's lip and jaw structure to produce said composite image.

* * * * *